US010912719B2

(12) United States Patent
Gulbin

(10) Patent No.: US 10,912,719 B2
(45) Date of Patent: Feb. 9, 2021

(54) PERSONAL CARE COMPOSITION AND METHOD OF MAKING

(71) Applicant: The Procter & Gamble Company, Cincinnati, OH (US)

(72) Inventor: Timothy Charles Gulbin, Maineville, OH (US)

(73) Assignee: The Procter and Gamble Company, Cincinnati, OH (US)

(*) Notice: Subject to any disclaimer, the term of this patent is extended or adjusted under 35 U.S.C. 154(b) by 225 days.

(21) Appl. No.: 14/881,714

(22) Filed: Oct. 13, 2015

(65) Prior Publication Data

US 2016/0106663 A1 Apr. 21, 2016

Related U.S. Application Data

(60) Provisional application No. 62/066,014, filed on Oct. 20, 2014.

(51) Int. Cl.
*A61K 8/97* (2017.01)
*A61K 8/46* (2006.01)
*A61Q 5/12* (2006.01)
*A61Q 5/02* (2006.01)
*A61K 8/02* (2006.01)
*A61K 8/92* (2006.01)

(52) U.S. Cl.
CPC .............. *A61K 8/027* (2013.01); *A61K 8/922* (2013.01); *A61Q 5/02* (2013.01); *A61K 2800/412* (2013.01); *A61K 2800/596* (2013.01); *A61K 2800/60* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 4,726,915 A * | 2/1988 | Verdicchio | A61K 8/442 424/70.19 |
| 5,609,862 A | 3/1997 | Chen et al. | |
| 5,776,444 A | 7/1998 | Birtwistle et al. | |
| 5,811,487 A | 9/1998 | Schulz, Jr. et al. | |
| 6,183,766 B1 | 2/2001 | Sine et al. | |
| 6,991,799 B2 | 1/2006 | Pham et al. | |
| 7,303,744 B2 | 12/2007 | Wells et al. | |
| 7,531,497 B2 | 5/2009 | Midha et al. | |
| 7,560,125 B2 | 7/2009 | Ananthapadmanabhan et al. | |
| 7,776,347 B2 | 8/2010 | Kerschner et al. | |
| 8,252,271 B2 | 8/2012 | Singer et al. | |
| 8,349,301 B2 | 1/2013 | Wells et al. | |
| 8,349,302 B2 | 1/2013 | Johnson et al. | |
| 8,361,448 B2 | 1/2013 | Johnson et al. | |
| 8,361,449 B2 | 1/2013 | Wells et al. | |
| 8,361,450 B2 | 1/2013 | Johnson et al. | |
| 8,367,048 B2 | 2/2013 | Wells et al. | |
| 8,470,305 B2 | 6/2013 | Johnson et al. | |
| 8,653,014 B2 | 2/2014 | Hilvert et al. | |
| 8,663,612 B2 | 3/2014 | Gamez-Garcia et al. | |
| 8,932,569 B2 | 1/2015 | Garrison et al. | |
| 8,940,285 B2 | 1/2015 | Leray et al. | |
| 9,138,429 B2 | 9/2015 | Wise et al. | |
| 9,381,382 B2 | 7/2016 | Schwartz et al. | |
| 2002/0131946 A1 | 9/2002 | Pham et al. | |
| 2003/0223952 A1 | 12/2003 | Wells et al. | |
| 2003/0224954 A1 | 12/2003 | Wells et al. | |
| 2004/0157754 A1 | 8/2004 | Geary et al. | |
| 2005/0112083 A1 | 5/2005 | Wells et al. | |
| 2005/0196368 A1 | 9/2005 | Laurent et al. | |
| 2005/0267258 A1 | 12/2005 | Rajaraman et al. | |
| 2006/0025256 A1 | 2/2006 | Wake | |
| 2006/0078524 A1 | 4/2006 | Midha et al. | |
| 2006/0078527 A1 | 4/2006 | Midha et al. | |
| 2006/0079419 A1 | 4/2006 | Wagner et al. | |
| 2006/0079420 A1 | 4/2006 | Wagner et al. | |
| 2006/0079421 A1 | 4/2006 | Wagner et al. | |
| 2006/0250658 A1 | 11/2006 | Jurgensen | |
| 2007/0110700 A1 | 5/2007 | Wells et al. | |
| 2008/0039352 A1 | 2/2008 | Wells et al. | |
| 2008/0096786 A1 | 4/2008 | Holt et al. | |
| 2008/0152611 A1 | 6/2008 | Wells et al. | |
| 2010/0061952 A1 | 3/2010 | Wells et al. | |
| 2010/0226868 A1 | 9/2010 | Gamez-Garcia et al. | |
| 2010/0234260 A1 | 9/2010 | Sekine et al. | |

(Continued)

FOREIGN PATENT DOCUMENTS

EP 1384467 B1 5/2007
FR 1971709 A1 8/2012

(Continued)

OTHER PUBLICATIONS

PCT International Search Report and Written Opinion for PCT/US2015/056423 dated Jan. 8, 2016.
Meirleir Niels De et al., "The rheological properties of hydrogenated castor oil crystals", Colloid & Polymer Science, Springer Verlag, Heidelberg, DE, vol. 292, No. 10, Jun. 12, 2014, pp. 2539-2547.
"Herbal Essence Shampoo", Mintel, Jun. 1, 2014.
All final and non-final office actions for U.S. Appl. No. 14/322,573.
All final and non-final office actions for U.S. Appl. No. 14/478,013.
All final and non-final office actions for U.S. Appl. No. 15/635,633.
All final and non-final office actions for U.S. Appl. No. 15/703,046.
All final and non-final office actions for U.S. Appl. No. 15/728,663.

(Continued)

*Primary Examiner* — Dominic Lazaro
(74) *Attorney, Agent, or Firm* — Angela K. Haughey

(57) ABSTRACT

This invention relates to an improved crystallization process of hydrogenated castor oil structurant which results in (i) a dispersion having a high concentration of the structurant, and (ii) a crystal habit/form that results in a higher yield stress in the final product, imparting high stability, for a given amount structurant. In addition, the resulting personal care product is consumer desired, as less structurant residue is observed on hair after the use of the personal care product.

20 Claims, No Drawings

(56) References Cited

U.S. PATENT DOCUMENTS

| | | |
|---|---|---|
| 2010/0322878 A1 | 12/2010 | Stella et al. |
| 2010/0330018 A1 | 12/2010 | Lorant et al. |
| 2011/0053818 A1 | 3/2011 | Chuchotiros et al. |
| 2011/0067720 A1 | 3/2011 | Ranade et al. |
| 2011/0070180 A1 | 3/2011 | Ranade et al. |
| 2011/0081392 A1 | 4/2011 | de Arruda et al. |
| 2011/0110991 A1 | 5/2011 | Garrison et al. |
| 2012/0164198 A1 | 6/2012 | Johnson et al. |
| 2012/0308502 A1 | 12/2012 | Wise et al. |
| 2012/0329768 A1* | 12/2012 | Wise ................. A61K 31/4365 514/188 |
| 2013/0090279 A1 | 4/2013 | Hilvert et al. |
| 2013/0131188 A1 | 5/2013 | Beckedahl et al. |
| 2013/0174863 A1 | 7/2013 | Marsh et al. |
| 2013/0243717 A1 | 9/2013 | Catalan et al. |
| 2013/0243835 A1 | 9/2013 | Tanner et al. |
| 2014/0018276 A1 | 1/2014 | Coffindaffer et al. |
| 2014/0051622 A1 | 2/2014 | De Meirleir |
| 2014/0162930 A1 | 6/2014 | De Meirleir |
| 2014/0162931 A1 | 6/2014 | De Meirleir |
| 2015/0011450 A1 | 1/2015 | Carter et al. |
| 2015/0059795 A1 | 3/2015 | Vatter et al. |
| 2015/0093422 A1 | 4/2015 | Garrison et al. |
| 2015/0342842 A1 | 12/2015 | Wise et al. |
| 2017/0333734 A1 | 11/2017 | Mauer et al. |
| 2017/0367955 A1 | 12/2017 | Brown et al. |

FOREIGN PATENT DOCUMENTS

| | | | |
|---|---|---|---|
| JP | 07258039 | 10/1995 | |
| WO | 96/25144 A1 | 8/1996 | |
| WO | WO9726854 A1 | 7/1997 | |
| WO | 9938489 A1 | 8/1999 | |
| WO | 2004/022681 A1 | 3/2004 | |
| WO | 2004/022682 A1 | 3/2004 | |
| WO | WO2010006866 A1 | 1/2010 | |
| WO | 2010/034736 A1 | 4/2010 | |
| WO | 2011/120799 A1 | 10/2011 | |
| WO | WO 2011120799 A1 * | 10/2011 | ............... C11D 1/66 |
| WO | WO2011134832 A2 | 11/2011 | |
| WO | 1WO2012175682 A2 | 12/2012 | |
| WO | WO2012175677 A2 | 12/2012 | |

OTHER PUBLICATIONS

Momentive SFE839 product brochure, <https://www.momentive.com/products/showtechnicaldatasheet.aspx?id=14443>available Sep. 2008; accessed Jul. 17, 2015.
PCT International Search Report and Written Opinion for PCT/US2014/045197 dated Oct. 7, 2014.
PCT International Search Report and Written Opinion for PCT/US2014/054294 dated Nov. 11, 2014.
PCT International Search Report and Written Opinion for PCT/US2017/039444 dated Aug. 28, 2017.
PCT International Search Report and Written Opinion for PCT/US2017/051249 dated Nov. 10, 2017.
U.S. Appl. No. 15/703,046, filed Sep. 13, 2017, Cochran et al.
U.S. Appl. No. 15/728,663, filed Oct. 10, 2017, Hutton, III et al.

* cited by examiner

PERSONAL CARE COMPOSITION AND METHOD OF MAKING

FIELD OF THE INVENTION

The present invention relates to a method of manufacturing a personal care composition, and the resulting personal care composition comprising a structurant.

BACKGROUND OF THE INVENTION

Personal care compositions often contain materials which provide stability to the composition. A stable personal care composition is important to consumers since a loss of stability leads to a separated product. Besides being aesthetically unattractive to consumers, a separated personal care composition can lead to products in which either the top or bottom layer of the composition is deficient in critical actives.

Stabilizing agents are typically crystallized out of a hot solution or an emulsion and then added to personal care products in order to improve product stability. Typically, the process of forming a concentrated premix composition comprising crystals of the desired crystal morphology is a two step process in which the stabilizing agent first diffuses from droplets in an emulsion into a solution where crystallization then occurs. This method is slow, costly, and can require ingredients that provide minimal or no functional value in the final personal care composition.

Accordingly, there is a need for a more efficient manufacturing process to crystallize stabilizing agents more efficiently for use in personal care compositions. In addition, there is a need for crystals with a morphology which imparts a greater stability to personal care compositions. Furthermore, there is a need for crystals which can be easily blended into the personal care composition in a timely and cost effective manner and which results in an improvement to stability without a significant increase in the materials added.

SUMMARY OF THE INVENTION

The invention relates to a method of making a personal care composition comprising the steps of: Preparing a premix composition by mixing from about 0.30% to about 4% of hydrogenated castor oil by weight of the premix composition, wherein the hydrogenated castor oil comprises of particles of which 90% by weight of the total hydrogenated castor oil consists of particle with size of less than 60 micrometers; from about 15% to about 40% of one or more surfactants, by weight of the premix composition; from about 60% to about 80% of an aqueous carrier by weight of the premix composition; adjusting the pH of the premix composition to about 5 to about 12; heating the premix composition to 65-84° C.; and then cooling the premix composition to a temperature of about 60° C. to about 20° C. Next a personal care composition is formed by combining the pre-mix with from about 5% to about 25% of detersive surfactant by weight of the personal care composition; from about 80% to about 95% of an aqueous carrier by weight of the personal care composition. The resulting personal care composition comprises from about 0.03% to about 1% of hydrogenated castor oil by weight of the personal care composition, and comprises crystals wherein from about 80 weight % to about 100 weight % of the resulting crystals have a fiber shape and wherein from about 80% to about 100% of the fiber shaped crystals are longer than about 5 micrometers.

The invention also relates to a personal care composition comprising from about 5 to about 25 wt % of an detersive surfactant; from about 1% to about 20% wt % of hydrogenated castor oil premix composition by weight of the personal care composition wherein the hydrogenated castor oil premix composition comprises: from about 0.30% to about 4% of hydrogenated castor oil by weight of the premix composition; from about 15% to about 40% of one or more surfactants, by weight of the premix composition; from about 60% to about 80% a aqueous carrier by weight of the premix composition; from about 80% to about 95% of an aqueous carrier by weight of the personal care composition. Wherein the personal care composition comprises from about 0.03% to about 1% of hydrogenated castor oil by weight of the personal care composition, and crystals wherein from about 80 weight % to about 100 weight % of the crystals have a fiber shape, and wherein from about 80% to about 100% of the fiber shaped crystals are longer than about 5 micrometers.

The invention also relates to a personal care composition comprising from about 5% to about 25% by weight of the personal are composition of a detersive surfactant; from about 0.30% to about 4% of hydrogenated castor oil by weight of the personal care composition; an aqueous carrier; wherein the personal care composition comprises crystals and wherein from about 80 weight % to about 100 weight % of the crystals have a fiber shape, and wherein from about 80% to about 100% of the fiber shaped crystals are longer than about 10 micrometers.

DETAILED DESCRIPTION OF THE INVENTION

While the specification concludes with claims particularly pointing out and distinctly claiming the invention, it is believed that the present invention will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC").

As used herein, "personal care compositions" includes products such as shampoos, shower gels, liquid hand cleansers, hair colorants, facial cleansers, laundry detergent, dish detergent, and other surfactant-based liquid compositions As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Premix Composition

An improved crystallization process of hydrogenated castor oil structurant (commercial name: Thixcin R, supplied by Elementis Specialties) has been developed. This process results in improved cost by producing (i) a dispersion having high concentration of the structurant (more efficient use of the plant vessels), and (ii) a crystal habit/form that results in a higher yield stress in the final product, imparting high stability, for a given amount structurant. In addition, as a result of needing less of the more effective structurant, less structurant residue is observed on hair after the use of the personal care product. This, along with improved conditioning agent, such as small particle silicone, improves conditioning and shine of consumers' hair.

To achieve a personal care composition comprising less structurant, while also delivering conditioning and shine to the hair of the consumers in use, a premix composition is formed by combining, under high shear, from about 0.30% to about 4% by weight of the premix composition of hydrogenated castor oil ("HCO") structurant, from about 15% to about 40% by weight of the premix composition of surfactant, and from about 60% to about 80 by weight of the premix composition of an aqueous solution such as water together and heating to from about 65° C. to about 84° C. and pH adjusting to from about 5 to about 12, alternatively from about 6 to about 8. The premix composition is then mixed for about 5-20 minutes. The premix composition is then cooled from about 60° C. to about 20° C. under low shear at a rate of from about 10 to about 1° C. per minute. The resulting premix composition forms crystals from the HCO. These crystals are fiber like in structure.

Alternatively, the premix composition can be cooled to a temperature of from about 45° C. to about 25° C., and/or to a temperature of from about 50° C. to about 20° C., in a vessel by cooling the walls of the vessel while mixing and wherein the rate of cooling is from about 10° C. per minute to about 1° C. per minute, and/or at a rate of from about 5° C. per minute to about 1° C. per minute.

Following an alternate process, such as the process disclosed by Unilever (WO2011120799) results in large aggregates of structurant rather than the desired dispersion containing crystals of the HCO in the shape of fibers. Further, if the process is modified so that the Initial Process Temperature is 88° C. (e.g. above the melting point of HCO) the resulting crystals are varied in shape and size, therefore not forming the desired number and shape of crystals. Additionally, structurant dispersions containing large particles are also produced when the process is modified so that the Initial Process Temperature is low (63° C.) and outside the range of 65-84° C.

As described herein the shape which provides the crystal shape that provides the most stability in the formulation have a fiber type shape. These fibers are found in the premix composition as well as in the finished product formula (e.g. the shampoo).Of the crystals present in the personal care composition from about 80 to about 100% are in a fiber shape. Additionally, from about 80% to about 100% of the fiber shaped crystals are about 5 micrometers or longer, alternatively from about 80% to about 100% of the fiber shaped crystals are about 10 micrometers or longer. The crystals can be from about 5, 10, 20, 30 micrometers and/or to about 200, 100, 50, 45, 40 and/or 30 micrometers in length. A suitable range for the fiber length includes about 10 to about 40 micrometers, alternatively about 20 to about 30 micrometers. A suitable range for the fiber width includes from about 0.5 micrometers to about 2.0 micrometers. Crystals with aspect ratio higher than 5× are also considered to have a fiber form. Alternatively the crystals can have an aspect ratio higher than 10×.

In Examples 1-3 the premix compositions formed have suitable levels of fiber shaped crystals. The process to make these premix compositions keep the initial heating of the premix composition to between about 64° C. and about 84° C., thereby not melting the HCO. In contrast, comparative Example 7 heats the premix composition to 88° C., which melts the HCO, and results in crystals that are not of uniform habit and size (nor resulting in a consistent fiber shape). It is contemplated that if the HCO melts, the droplets coalesce and form bigger droplets, and bigger droplets do not crystallize in the same manner as smaller droplets.

Additionally, the rate of cooling should be about 10° C. to about 1° C. per minute to aid in the formation of fiber shaped crystal of the desired number of length. It is also contemplated that by slow cooling (e.g. <1.0° C./minute), the resulting crystals are very thin and fragile. As the premix composition continues to be cooled, the crystals are unable to withstand much shear and, consequently, are broken apart into small pieces which do not provide much structuring.

A. Structurant

The structurant is included in the premix composition at a level of from about 0.3% to about 4.0% by weight of the premix composition. The structurant can also be included in the premix composition at a level of from about 0.4, 0.5, 0.6, 0.7, 0.8, 0.9, 1.0, 1.5% to about 4.0, 3.5, 3.0, 2.5, 2.0, 1.5% by weight of the premix composition. Structurants are materials or mixtures of materials which provide structure to personal care compositions independently from any structuring effect of the detersive surfactant of the composition. Structuring benefits result from increasing the yield stress of the composition which enables phase stability; that is, higher yield stress allow the suspension of particles or insoluble liquid droplets throughout the composition without significant settling of such particles or droplets toward the bottom of the container and/or without significant raising (creaming) of such particles or droplets toward the top of the container of the composition.

Many structurants are believed to operate by forming a network of interconnected solid structures having particular morphologies in the personal care composition. These solid structures may take a variety of physical forms. Non-limiting examples of typical physical or morphological forms include non-spherical elongated particles such as fibers, needles, ribbons, and mixtures thereof. It is believed that such non-spherical, elongated particles, provide the most efficient structure in liquids. Consequently, in some embodiments, crystals are in the form of fibers. Suitable structurants include, crystallizable glyceride esters, such as hydrogenated castor oil, a material that has very limited aqueous solubility. Castor oils include glycerides, especially triglycerides, comprising C10 to C 22 alkyl or alkenyl moieties which incorporate a hydroxyl group. Hydrogenation of castor oil produces hydrogenated castor oil by converting double bonds, which are present in the starting oil as ricinoleyl moieties. These moieties are converted to ricinoleyl moieties, which are saturated hydroxyalkyl moieties, e.g., hydroxystearyl. The hydrogenated castor oil (HCO) herein may, in some embodiments, be selected from: trihydroxystearin; dihydroxystearin; and mixtures thereof. The HCO may be processed in any suitable starting form, including, but not limited those selected from solid, molten and mixtures thereof. Useful HCO may have the following characteristics: a melting point of from about 40° C. to about 100° C., alternatively from about 65° C. to about 95° C.; and/or Iodine value ranges of from about 0 to about 5, alternatively from about 0 to about 4, and alternatively from about 0 to about 2.6. The melting point of HCO can measured using DSC: Differential Scanning Calorimetry.

Suitable HCO include those that are commercially available. Non-limiting examples of commercially available HCO suitable for use include: THIXCIN-R® (supplied by Elementis), which is supplied as a powder having small particles (99 weight % smaller than of 44 micrometers).

The invention is not intended to be directed only to the use of hydrogenated castor oil. Any other suitable crystallizable glyceride may be used. In one example, the structurant is substantially pure triglyceride of 12-hydroxystearic acid. This molecule represents the pure form of a fully hydrogenated triglyceride of 12-hydrox-9-cis-octadecenoic acid. In nature, the composition of castor oil may vary somewhat. Likewise hydrogenation procedures may vary. Any other suitable equivalent materials, such as mixtures of triglycerides wherein at least about 80% wt. is from castor oil, may be used. Exemplary equivalent materials comprise primarily, or consist of, triglycerides; or comprise primarily, or consist of, mixtures of diglycerides and triglycerides; or comprise primarily, or consist of, mixtures of triglyerides with diglycerides and limited amounts, e.g., less than about 20% wt. of the glyceride mixtures, of monoglycerides; or comprise primarily, or consist of, any of the foregoing glycerides with limited amounts, e.g., less than about 20% wt., of the corresponding acid hydrolysis product of any of said glycerides. A proviso in the above is that the major proportion, typically at least about 80% wt, of any of said glycerides is chemically identical to glyceride of fully hydrogenated ricinoleic acid, i.e., glyceride of 12-hydroxystearic acid. It is for example well known in the art to modify hydrogenated castor oil such that in a given triglyceride, there will be two 12-hydroxystearic-moieties and one stearic moiety. Likewise it is envisioned that the hydrogenated castor oil may not be fully hydrogenated. In contrast, the invention may exclude poly(oxyalkylated) castor oils when these fail the melting criteria.

B. Surfactant

The premix composition also comprises from about 15% to about 40%, alternatively from about 15, 20, 25% to about 40, 35, 30, 25% by weight of the premix composition of surfactant one or more surfactants. The one or more surfactants in turn may comprise an anionic surfactant, amphoteric, cationic or zwitterionic surfactants, or mixtures thereof. Various examples and descriptions of surfactants are set forth in U.S. Pat. No. 6,649,155; U.S. Patent Application Publication No. 2008/0317698; and U.S. Patent Application Publication No. 2008/0206355, which are incorporated herein by reference in their entirety.

Suitable anionic surfactants for use in the premix composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Personal Care Composition

A personal care composition is then formed by combining the premix composition with from about 5 to about 25% by weight of the personal care composition of detersive surfactant and from about 80 to about 95% by weight of the personal care composition aqueous carrier. Additional synthetic cationic polymers, conditioning agents and optional ingredients may also be included to form the personal care composition. For example the resulting product is a personal care cleansing composition including, but not limited to, a shampoo.

A. Detersive Surfactant

The personal care composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the personal care composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the personal care composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the personal care composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the personal care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present personal care composition include cocoamphoacetate, cocoamphodiacetate, lauroamphoacetate, lauroamphodiacetate, and mixtures thereof.

Zwitterionic detersive surfactants suitable for use in the personal care composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the personal care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The personal care composition may also comprise a silicone, cationic deposition aid, an aqueous carrier, and other additional ingredients described herein.

B. Optional Ingredients

In accordance with embodiments of the present invention, the personal care composition may further comprise one or more optional ingredients, including benefit agents Suitable benefit agents include, but are not limited to conditioning agents, cationic polymers silicone emulsions, anti-dandruff actives, gel networks, chelating agents, and, natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Conditioning Agents

The conditioning agent of the personal care compositions can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000;

from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent of the personal care compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Emulsifiers

A variety of anionic and nonionic emulsifiers can be used in the personal care composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Chelating Agents

The personal care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Levels of the EDDS chelant in the personal care compositions can be as low as about 0.01 wt % or even as high as about 10 wt %, but above the higher level (i.e., 10 wt %) formulation and/or human safety concerns may arise. In an embodiment, the level of the EDDS chelant may be at least about 0.05 wt %, at least about 0.1 wt %, at least about 0.25 wt %, at least about 0.5 wt %, at least about 1 wt %, or at least about 2 wt % by weight of the personal care composition. Levels above about 4 wt % can be used but may not result in additional benefit.

Gel Network

The personal care composition may also comprise fatty alcohol gel networks. These gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

The fatty alcohol can be included in the fatty alcohol gel network at a level by weight of from about 0.05 wt % to about 14 wt %. For example, the fatty alcohol may be present in an amount ranging from about 1 wt % to about 10 wt %, and/or from about 6 wt % to about 8 wt %.

The fatty alcohols useful herein include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 1 provides the components and their respective amounts for an example gel network composition.

TABLE 1

Gel network components

| Ingredient | Wt. % |
|---|---|
| Water | 78.27% |
| Cetyl Alcohol | 4.18% |
| Steary Alcohol | 7.52% |
| Sodium laureth-3 sulfate (28% Active) | 10.00% |
| 5-Chloro-2-methyl-4-isothiazolin-3-one, Kathon CG | 0.03% |

In accordance with embodiments of the present invention, the personal care composition may further comprise one or more benefit agents. Exemplary benefit agents include, but are not limited to, particles, colorants, perfume microcapsules, gel networks, and other insoluble skin or hair conditioning agents such as skin silicones, natural oils such as sun flower oil or castor oil. In an embodiment, the benefit agent is selected from the group consisting of: particles; colorants; perfume microcapsules; gel networks; other insoluble skin or hair conditioning agents such as skin silicones, natural oils such as sun flower oil or castor oil; and mixtures thereof.

Cationic Deposition Polymer

The personal care composition also comprises a cationic deposition polymer. These cationic deposition polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic deposition polymer can be a mixture of deposition polymers.

According to an embodiment of the present invention, the personal care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

According to one embodiment, the cationic guar polymer has a weight average M.Wt. of less than about 2.5 million g/mol, and has a charge density of from about 0.05 meq/g to about 2.5 meq/g. In an embodiment, the cationic guar polymer has a weight average M.Wt. of less than 1.5 million g/mol, or from about 150 thousand to about 1.5 million g/mol, or from about 200 thousand to about 1.5 million g/mol, or from about 300 thousand to about 1.5 million g/mol, or from about 700,000 thousand to about 1.5 million g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.7 meq/g.

According to one embodiment, the cationic guar polymer has a weight average M.Wt. of less than about 1 million g/mol, and has a charge density of from about 0.1 meq/g to about 2.5 meq/g. In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

In an embodiment, the composition comprises from about 0.01% to less than about 0.7%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

The cationic guar polymer may be formed from quaternary ammonium compounds. In an embodiment, the quaternary ammonium compounds for forming the cationic guar polymer conform to the general formula 1:

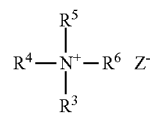

wherein where $R^3$, $R^4$ and $R^5$ are methyl or ethyl groups; $R^6$ is either an epoxyalkyl group of the general formula 2:

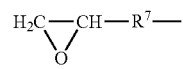

or $R^6$ is a halohydrin group of the general formula 3:

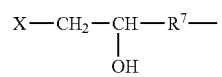

wherein $R^7$ is a $C_1$ to $C_3$ alkylene; X is chlorine or bromine, and Z is an anion such as Cl—, Br—, I— or $HSO_4$—.

In an embodiment, the cationic guar polymer conforms to the general formula 4:

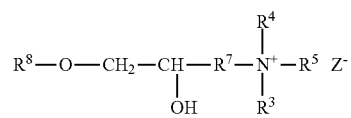

wherein $R^8$ is guar gum; and wherein $R^4$, $R^5$, $R^6$ and $R^7$ are as defined above; and wherein Z is a halogen. In an embodiment, the cationic guar polymer conforms to Formula 5:

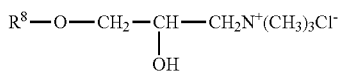

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Jaguar® C-17, which has a cationic charge density of about 0.6 meq/g and a M.Wt. of about 2.2 million g/mol and is available from Rhodia Company. Jaguar® C 13S which has a M.Wt. of 2.2 million g/mol and a cationic charge density of about 0.8 meq/g (available from Rhodia Company). Other suitable guar hydroxypropyltrimonium chloride are: guar hydroxypropyltrimonium chloride which has a charge density of about 1.1 meq/g and a M.Wt. of about 500,000 g/mole is available from ASI, a charge density of about 1.5 meq/g and a M.Wt. of about 500,000 g/mole is available from ASI. Other suitable guar hydroxypropyltrimonium chloride are: Hi-Care 1000, which has a charge density of about 0.7 meq/g and a M.Wt. of about 600,000 g/mole and is available from Rhodia; N-Hance 3269 and N-Hance 3270, which has a charge density of about 0.7 meq/g and a M.Wt. of about 425,000 g/mole and is available from ASI; N-Hance 3196, which has a charge density of about 0.8 and a M. Wt. Of about 1,100,000 g/mole and is available from ASI. AquaCat CG518 has a charge density of about 0.9 meq/g and a M.Wt. of about 50,000 g/mole and is available from ASI. BF-13, which is a borate (boron) free guar of charge density of about 1.1 meq/g and M. W.t of about 800,000 and BF-17, which is a borate (boron) free guar of charge density of about 1.7 meq/g and M. W.t of about 800,000 both available from ASI.

The personal care compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

In one embodiment of the invention, the non-guar galactomannan polymer derivatives have a M. Wt. from about 1,000 to about 10,000,000, and/or form about 5,000 to about 3,000,000.

The personal care compositions of the can also include galactomannan polymer derivatives which have a cationic charge density from about 0.5 meq/g to about 7 meq/g. In one embodiment of the present invention, the galactomannan polymer derivatives have a cationic charge density from about 1 meq/g to about 5 meq/g. The degree of substitution of the cationic groups onto the galactomannan structure should be sufficient to provide the requisite cationic charge density.

In one embodiment of the present invention, the galactomannan polymer derivative is a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

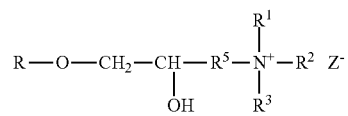

wherein R is the gum. The cationic galactomannan derivative can be a gum hydroxypropyltrimethylammonium chloride, which can be more specifically represented by the general formula 7:

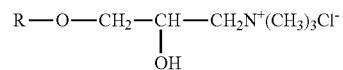

In another embodiment of the invention, the galactomannan polymer derivative is an amphoteric galactomannan polymer derivative having a net positive charge, obtained when the cationic galactomannan polymer derivative further comprises an anionic group.

In one embodiment of the invention the cationic non-guar galactomannan has a ratio of mannose to galactose is greater than about 4:1, a M.Wt. of about 100,000 to about 500,000, and/or from about 150,000 to about 400,000 and a cationic charge density from about 1 meq/g to about 5 meq/g, and/or from 2 meq/g to about 4 meq/g and is a derived from a *cassia* plant.

The personal care compositions of the present invention comprise at least about 0.05% of a galactomannan polymer derivative by weight of the composition. In one embodiment of the present invention, the personal care compositions comprise from about 0.05% to about 2%, by weight of the composition, of a galactomannan polymer derivative.

The personal care compositions of the present invention can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The personal care compositions of the present invention can comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the personal care compositions of the present invention have a molecular weight from about 850,000 to about 15,000,000 and/or from about 900,000 to about 5,000,000. As used herein, the term "molecular weight" refers to the weight average molecular weight. The weight average molecular weight may be measured by gel permeation chromatography ("GPC") using a Waters 600E HPLC pump and Waters 717 auto-sampler equipped with a Polymer Laboratories PL Gel MIXED-A GPC column (Part Number 1110-6200, 600.times 7.5 mm, 20 um) at a column temperature of 55.degree. C. and at a flow rate of 1.0 ml/min (mobile phase consisting of Dimethylsulfoxide with 0.1% Lithium Bromide), and using a Wyatt DAWN EOS MALLS (multi-angle laser light scattering detector) and Wyatt Optilab DSP (interferometric refractometer) detectors arranged in series (using a dn/dc of 0.066), all at detector temperatures of 50° C., with a method created by using a Polymer Laboratories narrow dispersed Polysaccharide standard (Mw=47,300), with an injection volume of 200 μl.

The personal care compositions of the present invention can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers of the present invention generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

In one embodiment of the present invention, cationically modified starch polymers are selected from degraded cationic maize starch, cationic tapioca, cationic potato starch, and mixtures thereof. In another embodiment, cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers in the present invention may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in compositions of the present invention is available from known starch suppliers. Also suitable for use in the present invention is nonionic modified starch that could be further derivatized to a cationically modified starch as is known in the art. Other suitable modified starch starting materials may be quaternized, as is known in the art, to produce the cationically modified starch polymer suitable for use in the invention.

Starch Degradation Procedure: In one embodiment of the present invention, a starch slurry is prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

(4) Cationic Copolymer of an Acrylamide Monomer and a Cationic Monomer

According to an embodiment of the present invention, the personal care composition comprises a cationic copolymer of an acrylamide monomer and a cationic monomer, wherein the copolymer has a charge density of from about 1.0 meq/g to about 3.0 meq/g. In an embodiment, the cationic copolymer is a synthetic cationic copolymer of acrylamide monomers and cationic monomers.

In an embodiment, the cationic copolymer comprises:
(i) an acrylamide monomer of the following Formula AM:

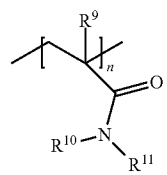

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

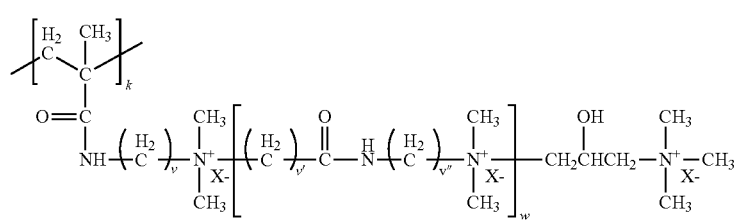

Formula CM where k=1, each of v, v', and v" is independently an integer of from 1 to 6, w is zero or an integer of from 1 to 10, and $X^-$ is an anion.

In an embodiment, cationic monomer conforming to Formula CM and where k=1, v=3 and w=0, z=1 and $X^-$ is $Cl^-$ to form the following structure:

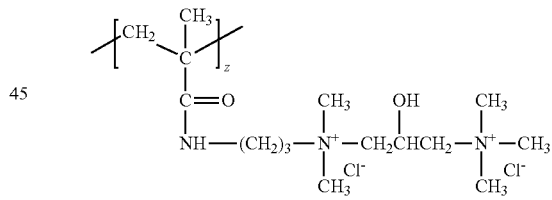

The above structure may be referred to as diquat. In another embodiment, the cationic monomer conforms to Formula CM and wherein v and v" are each 3, v'=1, w=1, y=1 and $X^-$ is $Cl^-$, such as:

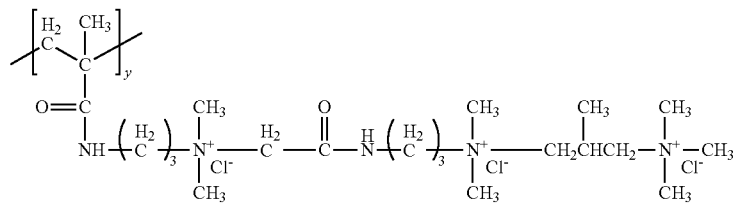

The above structure may be referred to as triquat.

In an embodiment, the acrylamide monomer is either acrylamide or methacrylamide.

In an embodiment, the cationic copolymer (b) is AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

In an alternative embodiment, the cationic copolymer is of an acrylamide monomer and a cationic monomer, wherein the cationic monomer is selected from the group consisting of: dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl(meth)acrylamide; ethylenimine, vinylamine, 2-vinylpyridine, 4-vinylpyridine; trimethylammonium ethyl (meth)acrylate chloride, trimethylammonium ethyl(meth) acrylate methyl sulphate, dimethylammonium ethyl(meth) acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, diallyldimethyl ammonium chloride, and mixtures thereof.

In an embodiment, the cationic copolymer comprises a cationic monomer selected from the group consisting of: cationic monomers include trimethylammonium ethyl (meth)acrylate chloride, trimethylammonium ethyl(meth) acrylate methyl sulphate, dimethylammonium ethyl(meth) acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, and mixtures thereof.

In an embodiment, the cationic copolymer is water-soluble. In an embodiment, the cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl(meth)acrylates with C1 to C3 in the alkyl and alkylene groups. In an embodiment, the cationized esters of the (meth)acrylic acid containing a quaternized N atom are selected from the group consisting of: ammonium salts of dimethylaminomethyl(meth)acrylate, dimethylaminoethyl (meth)acrylate, dimethylaminopropyl(meth)acrylate, diethylaminomethyl(meth)acrylate, diethylaminoethyl(meth) acrylate; and diethylaminopropyl(meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). In an embodiment, the cationic monomer when based on (meth)acrylamides are quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

In an embodiment, the cationic monomer based on a (meth)acrylamide is a quaternized dialkylaminoalkyl(meth) acrylamide with C1 to C3 in the alkyl and alkylene groups. In an embodiment, the cationic monomer based on a (meth) acrylamide is dimethylaminopropylacrylamide, which is quaternized with an alkyl halide, especially methyl chloride or benzyl chloride or dimethyl sulfate.

In an embodiment, the cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. In an embodiment, the cationic monomer is hydrolysis-stable and the hydrolysis-stable cationic monomer is selected from the group consisting of: diallyldimethylammonium chloride and water-soluble, cationic styrene derivatives.

In an embodiment, the cationic copolymer is a terpolymer of acrylamide, 2-dimethylammoniumethyl(meth)acrylate quaternized with methyl chloride (ADAME-Q) and 3-dimethylammoniumpropyl(meth)acrylamide quaternized with methyl chloride (DIMAPA-Q). In an embodiment, the cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

In an embodiment, the cationic copolymer has a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

In an embodiment, the cationic copolymer has a M.Wt. from about 100 thousand g/mol to about 2 million g/mol, or from about 300 thousand g/mol to about 1.8 million g/mol, or from about 500 thousand g/mol to about 1.6 million g/mol, or from about 700 thousand g/mol to about 1.4 million g/mol, or from about 900 thousand g/mol to about 1.2 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

According to an embodiment of the present invention, the personal care composition can comprise a cationic synthetic polymer that may be formed from
 i) one or more cationic monomer units, and optionally
 ii) one or more monomer units bearing a negative charge, and/or
 iii) a nonionic monomer,
wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers In one embodiment, the cationic polymers are water soluble or dispersible, non-crosslinked, and synthetic cationic polymers having the following structure:

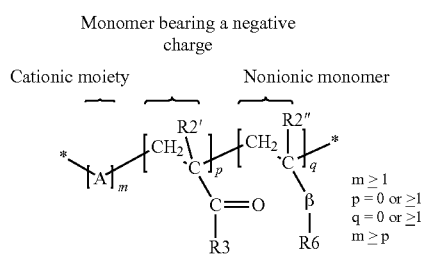

Monomer bearing a negative charge — Cationic moiety — Nonionic monomer $m \geq 1$
$p = 0$ or $\geq 1$
$q = 0$ or $\geq 1$
$m \geq p$ where A, may be one or more of the following cationic moieties:

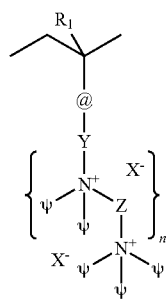

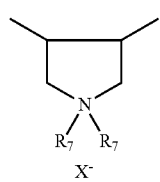

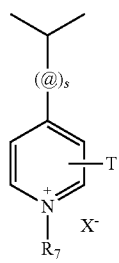

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl aryloxy;
where Z=C1-C22 alkyl, alkyloxy, aryl or aryloxy;
where R1=H, C1-C4 linear or branched alkyl;
where s=0 or 1, n=0 or 1;
where T and R7=C1-C22 alkyl; and
where X—=halogen, hydroxide, alkoxide, sulfate or alkylsulfate.

Where the monomer bearing a negative charge is defined by R2'=H, C1-C4 linear or branched alkyl and R3 as:

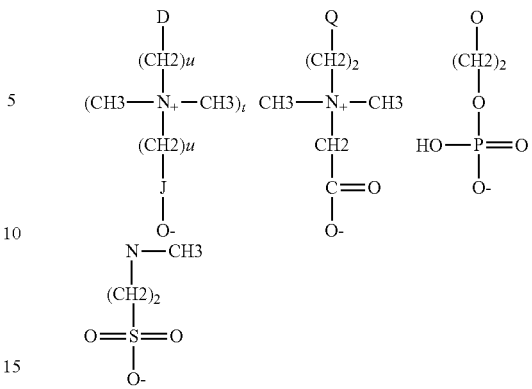

where D=O, N, or S;
where Q=$NH_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

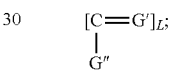

and
where G' and G" are, independently of one another, O, S or N—H and L=0 or 1.

Examples of cationic monomers include aminoalkyl (meth)acrylates, (meth)aminoalkyl(meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl(meth) acrylate methyl sulphate, dimethylammonium ethyl(meth) acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, diallyldimethyl ammonium chloride.

Suitable cationic monomers include those which comprise a quaternary ammonium group of formula —$NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl(meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride.

Additional suitable cationic monomers include trimethyl ammonium propyl(meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the personal care composition, or in a coacervate phase of the personal care composition, and so long as the counterions are physically and chemically compatible with the essential components of the personal care composition or do not otherwise unduly impair product performance, stability or aesthetics. Non limiting examples of such counterions include halides (e.g., chlorine, fluorine, bromine, iodine), sulfate and methylsulfate.

In one embodiment, the cationic polymer described herein aids in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the personal care composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable personal care composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. In some embodiments, the cationic charge density is about 6.2 meq/gm. The polymers also have a M. Wt. of from about 1,000 to about 5,000,000, and/or from about 10,000 to about 2,000,000, and/or from about 100,000 to about 2,000,000.

In another embodiment of the invention cationic synthetic polymers that provide enhanced conditioning and deposition of benefit agents but do not necessarily form lytropic liquid crystals have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M. Wt. of from about 1,000 to about 5,000,000, from about 10,000 to about 2,000,000, and from about 100,000 to about 2,000,000.

The concentration of the cationic polymers ranges about 0.025% to about 5%, from about 0.1% to about 3%, and/or from about 0.2% to about 1%, by weight of the personal care composition.

Suitable cationic cellulose polymers are salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Aqueous Carrier

The personal care compositions can be in the form of pourable liquids (under ambient conditions). Such compositions will therefore typically comprise a carrier, which is present at a level of from about 20 wt % to about 95 wt %, or even from about 60 wt % to about 85 wt %. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in embodiments of the personal care compositions of the present invention includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Product Form

The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions of the embodiments of the present invention may be hair tonics, leave-on hair products such as treatment, and styling products, rinse-off hair products such as shampoos and personal cleansing products, and treatment products; and any other form that may be applied to hair.

The personal care composition can have a viscosity of 4,000 cP to 20,000 cP, or from about 6,000 cP to about 12,000 cP, or from about 8,000 cP to about 11,000 cP, measured at 26.6° C. with a Brookfield R/S Plus Rheometer at $2\ s^{-1}$. cP means centipoises.

Test Methods

A. Optical Microscopy

Optical micrographs of the corresponding premix compositions are obtained by placing approximately 15 mg of sample of undiluted premix composition and observing via an optical microscope at 400× magnification.

B. Yield Stress Measurement

The yield stress of the samples are measured on a TA Instruments Discovery HR-3 rotational rheometer using a 60 mm 1° cone and plate geometry. The rheometer procedure applied comprised steps of
1. Bringing the sample to 25° C.
2. Executing a flow sweep from 1-0.001 1/s.
The yield stress value for each sample is calculated by plotting the log of the shear rate on the x-axis and the log of stress on the y-axis and fitting a Herschel-Bulkley model to the data.

C. Particle Size Measurement

The particle size of the Thixcin powder is measured using Alpine Jet Sieve, model A200LS, and a 325 mesh sieve. The particle size procedure is as follows 1. Weigh the sieve and record it as Weight A.
2. Weigh 20±0.01 g of the sample and place it on sieve.
3. Place sieve on Alpine Jet apparatus and run for one minute.
4. Clean material off lid and run for additional two minutes.
5. Weigh sieve and any material left on it together and record weight as Weight B. Calculate the % retained with the equation below:

% Retain=5×(Weight $B$−Weight $A$)

D. Fiber Characterization
Fiber Size

Thixcin dispersions (1.5% Thixcin concentration or alternate structurant) are diluted 1:25. Using a light microscope with an optical camera at a magnifying power of 400×, 15 fibers are measured for length and width in the premix solutions. This test can also be performed on personal are compositions to detect fiber size.

Fiber Percentage

Using a light microscope with an optical camera at a magnifying power of 200×, 15 sample fields, with dimensions of 430 um×22 mm, are viewed. All non-fiber particles within each of the samples are counted and measured. Due to the fact of the surfactant and Thixcin (or alternative structurant) have very similar densities, the % fibers in the samples are calculated using surface area using the equations below:

Sample Area=length×width of sample field

Total Thixcin Area=1.5% (amount of Thixcin in sample)×sample area

Non-fiber %=Total Non-fiber area/total Thixcin area

Fiber %=100−Non-fiber %

EXAMPLES

The following examples illustrate embodiments of the invention described herein. The exemplified personal care compositions can be prepared by conventional formulation and mixing techniques. It will be appreciated that other modifications of the personal care compositions, and/or conditioner compositions within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of Premix compositions, and Shampoo Compositions described herein.

| | Premix Composition | | | | |
|---|---|---|---|---|---|
| Ingredients | Example 1 | Example 2 | Example 3 | Example 4 | Example 5 |
| Hydrogenated Castor Oil (HCO)[1] | 1.5% | 0.5% | 1.5% | 1.5% | 1.5% |
| Sodium Lauryl Sulfate (SLS) (29% surfactant in water) | 98.15% | 99.1% | 98.1% | NA | 98.13% |
| Citric Acid | 0.35% | 0.4% | 0.4% | NA | 0.37% |
| Ammonium Lauryl Sulfate (ALS) (24% surfactant in water) | | | | 98.5% | |

-continued

| Ingredients | Premix Composition | | | | |
|---|---|---|---|---|---|
| | Example 1 | Example 2 | Example 3 | Example 4 | Example 5 |
| pH | 11 | 6.8 | 6.9 | 5.7 | 5.68 |
| Target Temperature | 80° C. | 75° C. | 80° C. | 80° C. | 80° C. |
| Above/Below Melting temperature of HCO | Below | Below | Below | Below | Below |
| Does any step in the process involve a clear solution of the structurant? | No | No | No | No | No |
| Cooling Rate | 2.5° C./min | 2.5° C./min | 2.5° C./min | 2.5° C./min | 1800° C./min |
| Shear Device | Cowles Blade 300 rpm for 20 minutes | Cowles Blade 300 rpm for 20 minutes | Cowles Blade 300 rpm for 20 minutes | Cowles Blade 300 rpm for 20 minutes | Quadro |
| Result | Good | Good | Good | Good | Good |
| Description | Majority of crystals observed were non-aggregated fibers of uniform size | Majority of crystals observed were non-aggregated fibers of uniform size | Majority of crystals observed were non-aggregated fibers of uniform size | Majority of crystals observed were non-aggregated fibers of uniform size | Majority of crystals observed were non-aggregated fibers of uniform size |
| Length of Fibers | Average = 28.9 micrometers Standard Deviation = 7.9 | | | | |
| Yield Stress | | 0.0784 Pascals | | 0.1430 Pascals | |

[1] Thixcin R supplied by Elementis.

Example 1

An amount of 7.5 g of HCO is dispersed in a solution of 1.75 g of citric acid and 491 g of SLS until no large agglomerates are visible. Dispersion is accomplished by using a Cowles blade at 300 rpm for 20 minutes. After dispersion, the mixture is heated to target temperature of 80° C. and held for 5-20 minutes. After temperature hold, the mixture is cooled at a rate of 2.5° C. /min to 30° C. under low shear.

Example 2

An amount of 2.5 g of HCO is dispersed in a solution of 2.0 g of citric acid and 495.5 g of SLS until no large agglomerates are visible. Dispersion is accomplished by using a Cowles blade at 300 rpm for 20 minutes. After dispersion, the mixture is heated to target temperature of 75° C. and held for 5-20 minutes. After temperature hold, the mixture is cooled at a rate of 2.5° C. /min to 30° C. under low shear.

Example 3

An amount of 7.5 g of HCO is dispersed in a solution of 2.0 g of citric acid and 491 g of SLS until no large agglomerates are visible. Dispersion is accomplished by using a Cowles blade at 300 rpm for 20 minutes. After dispersion, the mixture is heated to target temperature of 80° C. and held for 15-30 minutes. After temperature hold, the mixture is cooled at a rate of 2.5° C. /min to 30° C. under low shear.

Example 4

An amount of 7.5 g of HCO is dispersed in 491 g of ALS until no large agglomerates are visible. Dispersion is accomplished by using a Cowles blade at 300 rpm for 20 minutes. After dispersion, the mixture is heated to target temperature of 80° C. and held for 5-20 minutes. After temperature hold, the mixture is cooled at a rate of 2.5° C. /min to 30° C. under low shear.

Example 5

An amount of 3.6 Kg of HCO is dispersed in a solution of 0.888 Kg of citric acid and 235.4 Kg of SLS. Dispersion is accomplished by using a quadro. After dispersion, the mixture is heated to target temperature of 80° C. and held for 5-20 minutes. After temperature hold, the mixture is pumped through a cooling device into another vessel.

| Ingredients | Comp Example 1 | Comp Example 2 | Comp Example 3 | Comp Example 4 | Comp Example 5 |
|---|---|---|---|---|---|
| Hydrogenated Castor Oil (HCO)[1] | 1.5% | 1.75% | 1.75% | 0.39% | 0.39% |
| Sodium Lauryl Sulfate (SLS) (29% surfactant in water) | | 97.85% | 97.85% | | |

-continued

| Ingredients | Comp Example 1 | Comp Example 2 | Comp Example 3 | Comp Example 4 | Comp Example 5 |
|---|---|---|---|---|---|
| Sodium Laureth 1 Sulfate (SLE1S) (26% surfactant in water) | 98.15% | | | | |
| Citric Acid | 0.35% | 0.4% | 0.4% | | |
| AE3[2] | | | | 11.25% | |
| AE9[3] | | | | | 11.25% |
| Water | | | | 88.36% | 88.36% |
| pH | 6.8 | 6.7 | 6.8 | | 7.5 |
| Target Temperature | 80° C. | 63° C. | 88° C. | 84° C. | 84° C. |
| Above/Below Melting temperature of HCO | Below | Below | Above | Below | Below |
| Does any step in the process involve a clear solution of the structurant? | No | No | No | Yes | Yes |
| Cooling Rate | 0.8° C./min | 2.5° C./min | 2.5° C./min | 2.0° C./min | 2.0° C./min |
| Shear Device | Cowles Blade 300 rpm for 20 minutes | Cowles Blade 300 rpm for 20 minutes | Cowles Blade 300 rpm for 20 minutes | Stir bar | Stir Bar |
| Result Description | Poor No crystals observed | Poor Very few fiber crystals were observed. Most crystals observed were spherically or irregular in shape. | Poor Mixture of three crystal habits (fibers, spheres, irregular) of equal proportions | Poor Majority of the crystals are highly aggregated non-fiber (spherical, irregular) particles. The minority fiber crystals are also highly aggregated. | Poor 20-30% are small fibers while the other material is highly aggregated particles with irregular shape. |
| Yield Stress | | | 0.0102 Pascals | No Measurable yield stress | |

[2]Tomadol 25-3 supplied by Tomah Products
[3]Tergitol 15-s-9 supplied by Dow Chemical Comparative Example 1

An amount of 8.75 g of HCO is dispersed in a solution of 1.75 g of citric acid and 489.5 g of SLE1S until no large agglomerates are visible. Dispersion is accomplished by using a Cowles blade at 300 rpm for 20 minutes. After dispersion, the mixture is heated to target temperature of 80° C. and held for 15-30 minutes. After temperature hold, the mixture is cooled at a rate of 0.8° C. /min to 20° C. under low shear.

Comparative Example 2

An amount of 8.75 g of HCO is dispersed in a solution of 2.0 g of citric acid and 489.25 g of SLS until no large agglomerates are visible. Dispersion is accomplished by using a Cowles blade at 300 rpm for 20 minutes. After dispersion, the mixture is heated to target temperature of 63° C. and held for 5-20 minutes. After temperature hold, the mixture is cooled at a rate of 2.5° C./min to 20° C. under low shear.

Comparative Example 3

An amount of 8.75 g of HCO is dispersed in a solution of 2.0 g of citric acid and 489.25 g of SLS until no large agglomerates are visible. Dispersion is accomplished by using a Cowles blade at 300 rpm for 20 minutes. After dispersion, the mixture is heated to target temperature of 88° C. and held for 5-20 minutes. After temperature hold, the mixture is cooled at a rate of 2.5° C./min to 20° C. under low shear.

Comparative Example 4

An amount of 2.5 g of HCO is dissolved in 72.8 g of surfactant at 84° C. After dissolution, the solution is added to 572 g of water at 65° C. being mixed at 250 RPM. The solution is mixed under these conditions for 10 minutes. Then the mixing speed is reduced to 175 RPM and solution is mixed for an additional 30 minutes. The solution is then cooled to room temperature at a rate of 2° C./minute.

Comparative Example 5

An amount of 2.5 g of HCO is dissolved in 72.8 g of surfactant at 84° C. After dissolution, the solution is added to 572 g of water at 65° C. being mixed at 250 RPM. The solution is mixed under these conditions for 10 minutes. Then the mixing speed is reduced to 175 RPM and solution is mixed for an additional 30 minutes. The solution is then cooled to room temperature at a rate of 2° C./minute.

Shampoo Compositions

| Ingredient | Ex A | Ex B | Ex C | Ex D | Ex E | Ex F |
|---|---|---|---|---|---|---|
| Sodium lauryl ether sulfate (SLE3S) (1) | | 6 | | | | |
| Sodium lauryl sulfate (SLS) (2) | 1.5 | 7 | | | 1.5 | 1.5 |
| Sodium lauryl ether sulfate (SLE1S) (3) | 12 | | 14 | 14 | 12 | 12 |
| Cocamidopropyl betaine (CapB) (4) | 2 | 2 | 2 | 2 | 2 | 2 |
| Coconut monoethanol amide (CMEA) (5) | | 0.85 | | 0.85 | | |
| Stearyl alcohol (6)* | | | 1.29 | 1.29 | 1.29 | |
| Cetyl Alcohol (7)* | | | 0.71 | 0.71 | 0.71 | |
| Silicone (Dimethicone/Dimethiconol) (8) | 1 | 1 | 1 | 1 | 1 | 1 |
| Ethylene glycol distearate (EGDS) (9) | 1.5 | 1.5 | | | | |
| Hydrogenated Castor Oil (Trihydroxysterin) (10) | | | 0.1 | 0.1 | 0.1 | 0.1 |
| Guar Hydroxypropyltrimonium chloride (11) | 0.25 | 0.25 | 0.15 | 0.15 | 0.25 | 0.25 |
| Synthetic Cationic Polymer DADMAC (12) | | | 0.1 | 0.1 | | |
| Zinc pyrithione (13) | | | | | | 1 |
| Zinc carbonate (14) | | | | | | 1.61 |
| Water-USP Purified & Minors | Q.S. to 100 | Q.S. to 100 | Q.S. to 100 | Q.S. to 100 | Q.S. to 100 | Q.S. to 100 |

(1) Sodium Laureth-3 Sulfate from the Stepan Company
(2)) Sodium Lauryl Sulfate from Stepan Company
(3) Sodium Laureth-1 Sulfate from the Stepan Company
(4) Amphosol HCA from Stepan Company
(5) Ninol COMF from Stepan Company
(6) CO 1895 from Procter & Gamble
(7) CO 1695 from Procter & Gamble
(8) Silicone Belsil DM 5500 from Wacker Chemical Corp.
(9) EGDS from Goldschmidt Chemical Company
(10) Thixcin R from Elements
(11) Jaguar C500 from Rhodia
(12) Poly (Dially) Dimethyl Ammonium Chloride from Rhodia
(13) ZPT from Arch Chemical
(14) Zinc Carbonate from Bruggeman Group
*Fatty alcohol is added as part of the Gel Network

What is claimed is:

1. A method of making a stable personal care composition comprising the steps of:
   a. preparing a premix composition comprising hydrogenated castor oil, one or more surfactants and an aqueous carrier by
      1. mixing
         i. from about 0.30% to about 4% of the hydrogenated castor oil by weight of the premix composition, wherein the hydrogenated castor oil comprises particles of which 90% by weight of the total hydrogenated castor oil of the premix has particles with a size of less than 60 micrometers;
         ii. from about 15% to about 40% of the one or more surfactants selected from the group consisting of anionic surfactant, amphoteric, cationic or zwitterionic surfactants, and mixtures thereof, by weight of the premix composition;
         iii. from about 60% to about 80% of the aqueous carrier by weight of the premix composition;
      2. adjusting the pH of the premix composition to about 5 to about 12;
      3. heating the premix composition to 65-84° C., maintaining a temperature below the melting point of the hydrogenated castor oil;
      4. cooling the premix composition to a temperature of about 60° C. to about 20° C.;
   b. forming a personal care composition comprising the premix composition, detersive surfactants, and an aqueous carrier by combining the premix composition with
      1. from about 5% to about 25% of detersive surfactant by weight of the personal care composition;
      2. from about 80% to about 95% of an aqueous carrier by weight of the personal care composition;

wherein the personal care composition comprises from about 0.03% to about 1% of hydrogenated castor oil by weight of the personal care composition, and
   wherein the personal care composition comprises crystals resulting from the premix composition, and
   wherein from about 80 weight % to about 100 weight % of the crystals resulting from the premix composition have a fiber shape, and
   wherein from about 80% to about 100% of the fiber shaped crystals are longer than about 5 micrometers.

2. A method according to claim 1, wherein the personal care composition comprises from about 0.05% to about 0.5% of hydrogenated castor oil by weight of the personal care composition.

3. A method according to claim 2, wherein the personal care composition comprises from about 0.05% to about 0.15% of hydrogenated castor oil by weight of the personal care composition.

4. The personal care composition of claim 1, wherein from about 80% to about 100% of the fiber shaped crystals have a length of from about 5 micrometers to about 80 micrometers.

5. A method according to claim 4, wherein from about 80% to about 100% of the fiber shaped crystals have a length of from about 10 micrometers to about 50 micrometers.

6. A method according to claim 5, wherein from about 80% to about 100% of the fiber shaped crystals have a length of from about 20 micrometers to about 40 micrometers.

7. A method according to claim 1, wherein the cooling of the premix composition of step a.4 is cooled to a temperature of 50° C. to about 20° C. is performed in a vessel by cooling the walls of the vessel while mixing and wherein the rate of cooling is from about 10° C. per minute to about 1° C. per minute.

8. A method according to claim 1, wherein the cooling of the premix composition of step a.4 is cooled to a temperature of about 45° C. to about 25° C. is performed in a vessel by cooling the walls of the vessel while mixing and wherein the rate of cooling is from about 10° C. per minute to about 1° C. per minute.

9. A method according to claim 1, wherein the cooling of the premix composition of step a.4 is cooled to a temperature of about 40° C. to about 30° C. is performed in a vessel by cooling the walls of the vessel while mixing and wherein the rate of cooling is from about 10° C. per minute to about 1° C. per minute.

10. A method according to claim 1, wherein the cooling of the premix composition of step a.4 is cooled to a temperature of about 50° C. to about 20° C. is performed in a vessel by cooling the walls of the vessel while mixing and wherein the rate of cooling is from about 5° C. per minute to about 1° C. per minute.

11. A method according to claim 1, wherein the cooling of the premix composition of step a.4 is cooled to a temperature of about 50° C. to about 20° C. is performed by passing the mixture through a cooling device and collecting it in a different vessel.

12. A method according to claim 1, wherein the cooling of the premix composition of step a.4 is cooled to a temperature of about 50° C. to about 20° C. is performed by passing the mixture through a cooling device and recirculating it back into the same vessel until the desired vessel temperature is achieved.

13. The method of claim 1, wherein the personal care composition further comprises from about 0.1% to about 0.25% by weight of the personal care composition, of a cationic guar polymer.

14. The method of claim 1, wherein the personal care composition further comprises from about from about 0.1% to about 1.5% by weight, of a conditioning agent.

15. The method of claim 1, wherein the one or more surfactants of the premix composition comprise from about 20% to about 35% by weight of the premix composition of a detersive surfactant, and wherein the detersive surfactant is an anionic surfactant.

16. The method of claim 15, wherein the anionic surfactant is SLE1S.

17. The method of claim 15, wherein the anionic surfactant is SLS.

18. A method of making a personal care composition comprising the steps of:
   a. preparing a premix composition comprising hydrogenated castor oil, one or more surfactants and an aqueous carrier by
      1. mixing
         i. from about 0.30% to about 4% of the hydrogenated castor oil by weight of the premix composition, wherein the hydrogenated castor oil comprises particles of which 90% by weight of the total hydrogenated castor oil has particles with a size of less than 60 micrometers;
         ii. from about 15% to about 40% of the one or more surfactants wherein the surfactant is selected from SLS, SLE1S and combinations thereof, by weight of the premix composition;
         iii. from about 60% to about 80% of the aqueous carrier by weight of the premix composition;
      2. adjusting the pH of the premix composition to about 5 to about 12;
      3. heating the premix composition to from 65 to about 84° C.;
      4. cooling the premix composition to a temperature of about 60° C. to about 20° C.;
   b. forming a personal care composition comprising the premix composition, detersive surfactants, and an aqueous carrier by combining the premix composition with
      1. from about 5% to about 25% of detersive surfactant by weight of the personal care composition;
      2. from about 80% to about 95% of an aqueous carrier by weight of the personal care composition;
wherein the personal care composition comprises crystals resulting from the premix composition, and
wherein from about 80 weight % to about 100 weight % of the crystals resulting from the premix composition have a fiber shape, and
wherein from about 80% to about 100% of the fiber shaped crystals are longer than about 5 micrometers.

19. The method of making a personal care composition of claim 18, wherein the premix is heated to from about 75° C. to about 84° C.

20. The method of making a personal care composition of claim 19, wherein the premix is heated to from about 80° C. to about 84° C.

* * * * *